(12) United States Patent
Fridzon

(10) Patent No.: US 10,524,884 B2
(45) Date of Patent: Jan. 7, 2020

(54) CONICAL CONNECTION FOR A DENTAL IMPLANT

(71) Applicant: Boris Fridzon, Petach Tikva (IL)

(72) Inventor: Boris Fridzon, Petach Tikva (IL)

(*) Notice: Subject to any disclaimer, the term of this patent is extended or adjusted under 35 U.S.C. 154(b) by 0 days.

(21) Appl. No.: 15/110,744

(22) PCT Filed: Jan. 12, 2015

(86) PCT No.: PCT/IL2015/050042
§ 371 (c)(1),
(2) Date: Jul. 10, 2016

(87) PCT Pub. No.: WO2015/104714
PCT Pub. Date: Jul. 16, 2015

(65) Prior Publication Data
US 2016/0317252 A1 Nov. 3, 2016

(30) Foreign Application Priority Data

Jan. 13, 2014 (IL) .......................................... 230438

(51) Int. Cl.
*A61C 8/00* (2006.01)
*A61B 6/14* (2006.01)
*A61B 90/00* (2016.01)

(52) U.S. Cl.
CPC .............. *A61C 8/0066* (2013.01); *A61B 6/14* (2013.01); *A61B 2090/3966* (2016.02); *A61C 8/0068* (2013.01); *A61C 8/0069* (2013.01)

(58) Field of Classification Search
CPC .... A61C 8/005–0074; A61C 2201/005; A61B 6/14; A61B 2090/3966

USPC .................................................. 433/172–176
See application file for complete search history.

(56) References Cited

U.S. PATENT DOCUMENTS

| 5,208,845 | A | 5/1993 | Gelb |
| 5,538,424 | A | 7/1996 | Gelb |
| 5,622,499 | A | 4/1997 | Simmons |
| 5,927,979 | A * | 7/1999 | Misch .................. A61C 8/0022 433/172 |
| 6,068,480 | A | 5/2000 | Misch et al. |
| 7,090,494 | B2 | 8/2006 | Shelemay et al. |

(Continued)

FOREIGN PATENT DOCUMENTS

| EP | 0231838 A2 | 8/1987 |
| KR | 20100011109 A | 2/2010 |

(Continued)

OTHER PUBLICATIONS

NobelActive™ Conical Connection Impression techniques—implant level, 2011, Nobel Biocare USA, LLC. 22715 Savi Ranch Parkway, Yorba Linda, CA 92887, www.nobelbiocare.com, 72138 Rev. 02 (Apr. 2011).

(Continued)

*Primary Examiner* — Matthew M Nelson
(74) *Attorney, Agent, or Firm* — The Roy Gross Law Firm, LLC; Roy Gross

(57) ABSTRACT

A dental device having an abutment body including a substantially radial mark on its external part, the abutment body adapted, to be connected, to an implant by a connecting member, such that the substantially radial mark is distinguishable from the abutment body in an image taken by an imaging device when the implant and abutment are installed.

19 Claims, 6 Drawing Sheets

(56) References Cited

U.S. PATENT DOCUMENTS

| | | | |
|---|---|---|---|
| 7,163,398 B2 | 1/2007 | Klardie et al. | |
| 7,204,692 B2 | 4/2007 | Klardie et al. | |
| 8,328,556 B2* | 12/2012 | Scommegna | A61C 8/005 433/172 |
| 2007/0259315 A1 | 11/2007 | Last-Pollak | |
| 2008/0097458 A1 | 4/2008 | Donahoe et al. | |
| 2008/0241789 A1* | 10/2008 | Mundorf | A61C 8/0018 433/173 |
| 2008/0280255 A1* | 11/2008 | D'Alise | A61C 8/0025 433/174 |
| 2011/0008752 A1 | 1/2011 | Schaffran et al. | |
| 2011/0229850 A1 | 9/2011 | Bretton et al. | |
| 2011/0306008 A1 | 12/2011 | Suttin et al. | |
| 2012/0251974 A1 | 10/2012 | Katz | |
| 2012/0295226 A1* | 11/2012 | Robb | A61C 8/008 433/201.1 |
| 2012/0301850 A1* | 11/2012 | Sollberger | A61C 8/005 433/174 |
| 2013/0108985 A1* | 5/2013 | Amber | A61C 8/0001 433/173 |
| 2013/0288202 A1* | 10/2013 | Hochman | A61C 8/008 433/175 |

FOREIGN PATENT DOCUMENTS

| | | |
|---|---|---|
| WO | 2012066524 A1 | 5/2012 |
| WO | 2012066524 A2 | 5/2012 |
| WO | 2013014643 A2 | 1/2013 |
| WO | 2013106542 A | 7/2013 |
| WO | 2013106542 A1 | 7/2013 |

OTHER PUBLICATIONS

Impression techniques, implant level—for conical connection implants Closed tray and open tray quick guide; Nobel Biocare USA, LLC. 22715 Savi Ranch Parkway, Yorba Linda, CA 92887, www.nobelbiocare.com, 72138 Rev. 02 (Apr. 2011). 72138 Rev. 04 (May 2012).

NobelActive™ Quick Start for Conical Connection; Nobel Biocare USA, LLC. 22715 Savi Ranch Parkway, Yorba Linda, CA 92887, www.nobelbiocare.com.

Eric Waites, Essentials of Radiography and Radiology, 2003, 444 pages, 3rd Edition, Churchill Livingston, An imprint of Elsevier Science Limited, ISBN 0443-07027-X.

D. Lingeshwar, et al., Diagnostic Imaging in Implant Dentistry, International Journal of Oral Implantology and Clinical Research, Sep.-Dec. 2010;1(3)147-153.

Deborah Meleo, et al., Fixture-abutment connection surface and micro-gap measurements by 3D micro-tomographic technique analysis, Ann Ist Super Sanità 2012 | vol. 48, No. 1: 53-58, DOI: 10.4415/ANN_12_01_09.

Product Catalog 2012, Nobel Biocare USA, LLC., 2012, 420 pages, 22715 Savi Ranch Parkway, Yorba Linda, CA 92887, www.nobelbiocare.com 72138 Rev. 04 (May 2012).

Basic Information on the Surgical Procedure, Straumann (R) Dental Implant System, 2007, 7 pages, Institut Straumann AG, Peter Marian-Weg 12, CH-4002 Basel Switzerland.

Michel Aislan Dantas Soares, et al., Comparative Study between three different conections for dental implants: Internal Hexagon, External Hexagon and Morse Taper, 20th International Congress of Mechanical Engineering, Nov. 15-20, 2009, 10 pages, Gramado, RS, Brazil.

E. Dwayne Kartateew, The Conical Cone Connection: The Essence of Mastering Implant Esthetics (Part 1), Oral Health Group, Apr. 1, 2010, 80 Valleybrook Drive Toronto, ON, M3B 2S9, Canada (http://www.oralhealthgroup.com/features/the-conical-cone-connection-the-essence-of-mastering-implant-esthetics-part-1/).

Philippe Hernigou, et al., One hundred and fifty years of history of the Morse taper: from Stephen A. Morse in 1864 to complications related to modularity in hip arthroplasty., May 30, 2013, International Orthopaedics (SICOT) (2013) 37:2081-2088, DOI 10.1007/s00264-013-1927-0, Springer-Verlag Berlin Heidelberg, DE.

Plug and Ring Gauges for Self-holding Tapers (Metrology), What-When-How—In Depth Tutorials and Information, 6 pages, accessed Jan. 22, 2017, (http://what-when-how.com/metrology/plug-and-ring-gauges-for-self-holding-tapers-metrology/).

Detlev Krechlok, Reaming—Course: Techniques for Machining of Material. Trainees' Handbook of Lessons, 21 pages, (accessed Jul. 2016, http://collections.infocollections.org/ukedu/en/d/Jgtz102be/) Institut fufliche Entwicklung e.V., Parkstra 23, 13187 Berlin, DE.

Tapers and Taper Problems, Riten Industries, Inc., 1100 Lakeview Avenue, Washington Court House, Ohio 43160, (accesed Jul. 2016, http://www.riten.com/technical-support/tapers-and-taper-problems/), 4 pages.

Specification for Plug and Ring Gauges for Self Holding Tapers, Apr. 1987, Bureau of Indian Standards Manak Bhavan, 9 Bahadur Shah Zafar Marg, New Delhi 110002, 11 pages.

International Search Report for PCT/IL2015/050042 completed Apr. 6, 2015; dated Apr. 6, 2015 1 Page.

Witten Opinion for PCT/IL2015/050042 Completed Apr. 6, 2015; dated Apr. 6, 2015 5 Pages.

Meleo et al; "Fixture-abutment connection surface and micro-gap measurements by 3D micro-tomographic technique analysis"; Ann Ist Super Sanità 2012 | vol. 48, No. 1: 53-58 DOI: 10.4415/ANN_12_01_09.

"Performance of conical abutment (Morse Taper) connection implants: a systematic review"; Journal of Biomedical Materials Research Part A, Feb. 2014 DOI: 10.1002/jbm.a.34709—Source: PubMed.

"Comparative Study between three different conections for dental implants:Internal Hexagon, External Hexagon and Morse Taper"; 20th International Congress of Mechanical Engineering copyright© 2009 by ABCM Nov. 15-20, 2009, Gramado, RS, Brazil.

"One hundred and fifty years of history of the Morse taper: from Strphen A. Morse in 1864 to complications related to modularity in hip arthroplasty"; International Orthopaedics (SICOT) (2013) 37:2081-2088 DOI 10.1007/s00264-013-1927-0.

Lingeshwar, et al. "Diagnostic Imaging in Implant Dentistry"; International Journal of Oral Implantology and Clinical Research, Sep.-Dec. 2010;1(3):147-153.

"Diagnostic Imaging in Implant Dentistry"—Noble Biocare.

Eric Whaites, "Essentials of Dental Radiography and Radiology." http://www.straumann.ca/en/professionals/products-and-solutions/surgical-and-restorative-solutions/one-system/soft-tissue-level-solutions/connection.html.

"Plug and Ring Gauges for Self-holding Tapers (Metrology)." http://what-when-how.com/metrology/plug-and-ring-gauges-for-self-holding-tapers-metrology/.

http://www.riten.com/technical-support/tapers-and-taper-problems/.

NobelActive™ Conical Connection Impression techniques—implant level.

Karateew, https://www.oralhealthgroup.com/features/the-conical-cone-connection-the-essence-of-mastering-implant-esthetics-part-1/.

Schmitt, et al.; "Performance of conical abutment (Morse Taper) connection implants: A systematic review", Journal of Biomedical Materials Research Part A—Feb. 2014 DOI: 10.1002/jbm.a.34709—Source: PubMed.

Specification for Plug and Ring Gauges for Self Holding Tapers; ( First Revision ), ( First Reprint Dec. 1993).

Detlev Krechlok; "Arbeitsmaterial f Lernenden Reiben".

* cited by examiner

CONICAL CONNECTION FOR A DENTAL IMPLANT

TECHNICAL FIELD

The present disclosure relates to dentistry in general, and to a device and method for making and using an abutment for a dental implant, in particular.

BACKGROUND

A dental implant is a device used in dentistry to support restorations, wherein the restorations resemble a tooth or group of teeth that replace missing teeth.

Most dental implants used today are formed similarly to an actual tooth root, and are sometimes referred to as having a "root-form". An implant is placed within the bone of the jaw, which then undergoes osseointegration with the implant. Osseointegration refers to the fusion of the implant surface with the surrounding bone.

Dental implants can be used to support one or more dental prostheses, including crowns, implant-supported bridges or dentures.

Once the implant is fixed within the patient's jaw bone, the process may continue with placing an abutment within the implant, upon which the crown, which comprises the visible part of the tooth or multiple teeth, may be installed. Thus, the abutment connects the implant to the crown and provides stability for the dental prosthetic.

The bottom part of the abutment is shaped so as to be inserted tightly into the implant, and its top part is shaped to receive the crown.

In recent years, implants having conical openings and corresponding conical abutments have gained increased popularity. In such configurations, the abutment comprises a screw and the implant may comprise a dowel, for connecting to each other.

A major factor in the quality of the prosthesis is the exact direction, strength and stability of the connection between the implant and the abutment. It is thus required to ensure that this connection is made in the correct angle and as strong and stable as possible, but not too strong to damage the implant.

BRIEF SUMMARY

One aspect of the disclosure relates to a device, comprising: an abutment body comprising a substantially radial mark on its external part, the abutment body adapted to be connected to an implant by a connecting member, wherein the substantially radial mark is distinguishable from the abutment body in an image taken by an imaging device when the implant and abutment are installed. Within the dental device, the radial mark optionally comprises a band made of a different material than the wrapper member. Within the dental device, the radial mark optionally comprises engraving in the wrapper member. Within the dental device, the radial mark is optionally aligned with a line of the implant when the dental abutment is inserted properly into the implant. Within the dental device, the line of the implant is optionally a level of an opening in the implant. Within the dental device, the line of the implant is optionally a substantially horizontal mark on an external part of the implant. Within the dental device, the imaging device is optionally an X-ray imager. Within the dental device, the dental abutment is optionally a conical dental abutment. Within the dental device, the connecting member is optionally a screw.

Another aspect of the disclosure relates to a method for installing an abutment in a dental implant, comprising: placing an abutment comprising a substantially radial mark on its external part into an implant and connecting the abutment to the implant by a connecting member; receiving an image of the implant and abutment; determining whether the substantially radial mark is aligned with a line of the implant; and responsive to the substantially radial mark not being aligned with the line of the implant, removing the abutment. Within the method, the radial mark optionally comprises a band made of a different material than the wrapper member. Within the method, the radial mark optionally comprises engraving in the wrapper member. Within the method, the radial mark is optionally aligned with a line of the implant when the dental abutment is inserted properly into the implant. Within the method, the line of the implant is optionally a level of an opening in the implant. Within the method, the line of the implant is optionally a substantially horizontal mark on an external part of the implant. Within the method, the imaging device is optionally an X-ray imager. Within the method, the dental abutment is optionally a conical dental abutment. Within the method, the connecting member is optionally a screw.

BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

One technical problem dealt with by the disclosed subject matter relates to the insertion of an abutment, and in particular a conical abutment into an implant. An abutments may be described as implant cap which functions as the base of the crown, and which comprises or receive a screw that connects it toteh implant. The implant is usually located in the jaw bone, and the abutment is placed into the implant. A screw, which may be supplied with the implant or separately is then screwed through the abutment into a screw holder area of the implant, and the crown is then attached to the top part of the screw.

Conical connections between the abutment and the implant usually provide better fitting and better control of the insertion of the abutment into the implant. By slowly turning the screw, the physician can control how deep the abutment is inserted into the implant. Better fitting provides for eliminating gaps which may cause infections.

Figure 1:
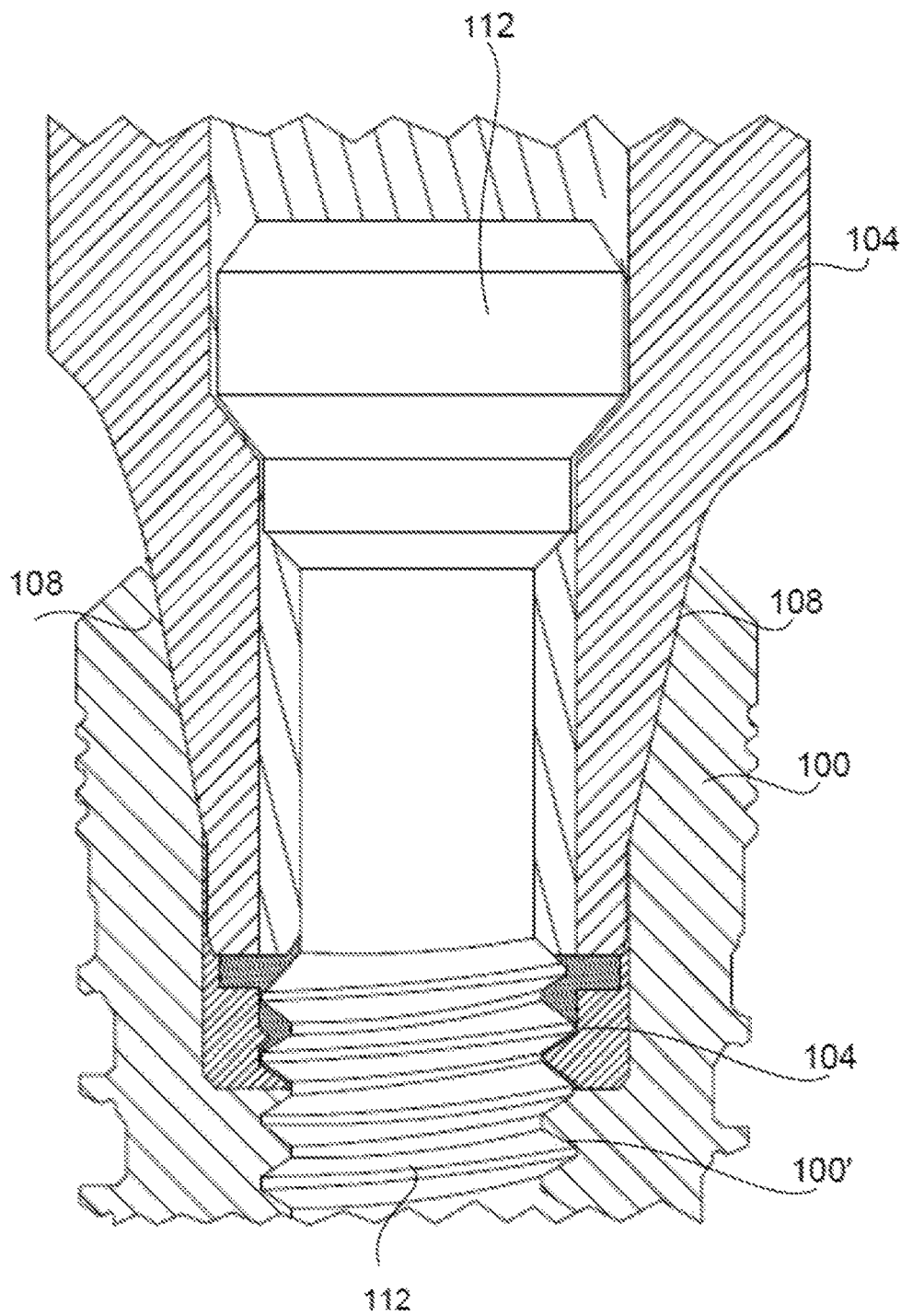
FIG. 1 is a schematic illustration of a cross section of an implant and a prior art conical abutment.

Referring now to FIG. 1 showing a schematic illustration of a cross section of an implant and a prior art abutment.

An implant 100 is implanted into the patient's jaw bone. The implant may or may not exceed the bone level. Implant 100 has an opening 108, wherein the external part of the opening is shaped as a truncated cone 108. The lower part of the opening is a screw anchor or dowel 100'.

A conical abutment comprising an abutment body 104 (for convenience referred to as "abutment") may then be inserted into the implant, after which a screw 112 or another connecting member can be inserted and screwed into screw anchor 100' of the implant. The crown of one or more teeth can be inserted into the main column area 112' of the screw.

Conical abutment 104 may be designed with a slope shaped to fit opening 108 of implant 100.

A screw 112 having a screw area and a main column 112' to which the crown may connect, is inserted through abutment 104 and fits into the screw anchor 100' of implant 100 and screw anchor 104' of abutment 104.

The implant external surface is often made rough, so as to assist the bone healing and intertwining with the implant. However, the rough surface may also prove as an ideal platform for bacterial growth. Combined with a potential gap between the abutment and the implant, this may cause serious problems down the road.

It will be appreciated that the conical contact area between the implant and the abutment gives the physician control over how deep to insert the abutment into the implant.

By applying the required torque when screwing screw 112, the physician can make sure that the abutment is inserted to the required depth into the implant. Correctly fitting the abutment into the implant provides for tight contact, thus eliminating undesired gaps between the abutment and the implant.

However, even when the physician applies the correct torque according to a device he or she is using, the screwing device may not be calibrated precisely enough and may not show the actual torque applied, resulting in under screwing the abutment and thus weakening the contact between the implant and the abutment and creating gaps. In other situations the abutment may be over screwed into the implant, thus activating excess forces and weakening the implant. In yet other situations, the abutment may not be initially placed in a perfectly horizontal position and may thus be inserted at an angle to the required direction, which may also create undesired gaps.

Currently, since the process is performed inside the person's gums, the physician has no visual feedback of the insertion, and has no way of verifying that the abutment is inserted correctly, is at the correct depth, and is leveled.

Thus it is required to provide an abutment and a method for verifying that the abutment is well fitted to the implant, such that it is not required to apply further torque and risk breaking the implant on one hand, but ensuring that no gap is left between the conical connections of the implant and the abutment, on the other hand.

Therefore, there is thus provided in accordance with some embodiments of the disclosure, an abutment with a substantially horizontal radial mark on the external part of the abutment. The mark may be located such that when the abutment is inserted correctly, the mark is at the same level as the opening of the implant. The opening may refer to the top rim of the implant when installing implants in the lower jaw and the bottom rim of the implant when installing implants in the upper jaw. The mark may be made such that it is visible in a frontal image of the patient's mouth area. For example, if the area is imaged with an X-ray imaging device, the mark may be engraved on the external part of the abutment, or may be made of another material attached to the abutment, wherein the other material seems different from the abutment material in an X-ray image. The mark may be shaped as a radial line or strip surrounding the abutment at the required height, a dashed line, a wave or zigzag shaped engraving, or the like. If the imaging equipment is color sensitive, the mark may be made to appear in different color, or in any other manner that will show the mark in the image. In some embodiments the mark may be radial and may wrap the abutment, while in other embodiments it may be marked only on parts of the perimeter of the abutment.

Thus, the physician can be careful with the amount of force applied when screwing the screw connecting the abutment to the implant. The physician may then take an image, and check whether the mark is at the same level as the opening of the implant. If it is, then the abutment is inserted correctly. If the mark is higher than the external rim of the implant (in the case of lower jaw implant), the physician may tighten the screw so that the abutment penetrates deeper into the implant. If the mark appears deeper into the jaw than the implant, then the physician may release the screw so as to avoid breaking the implant.

Figure 2:
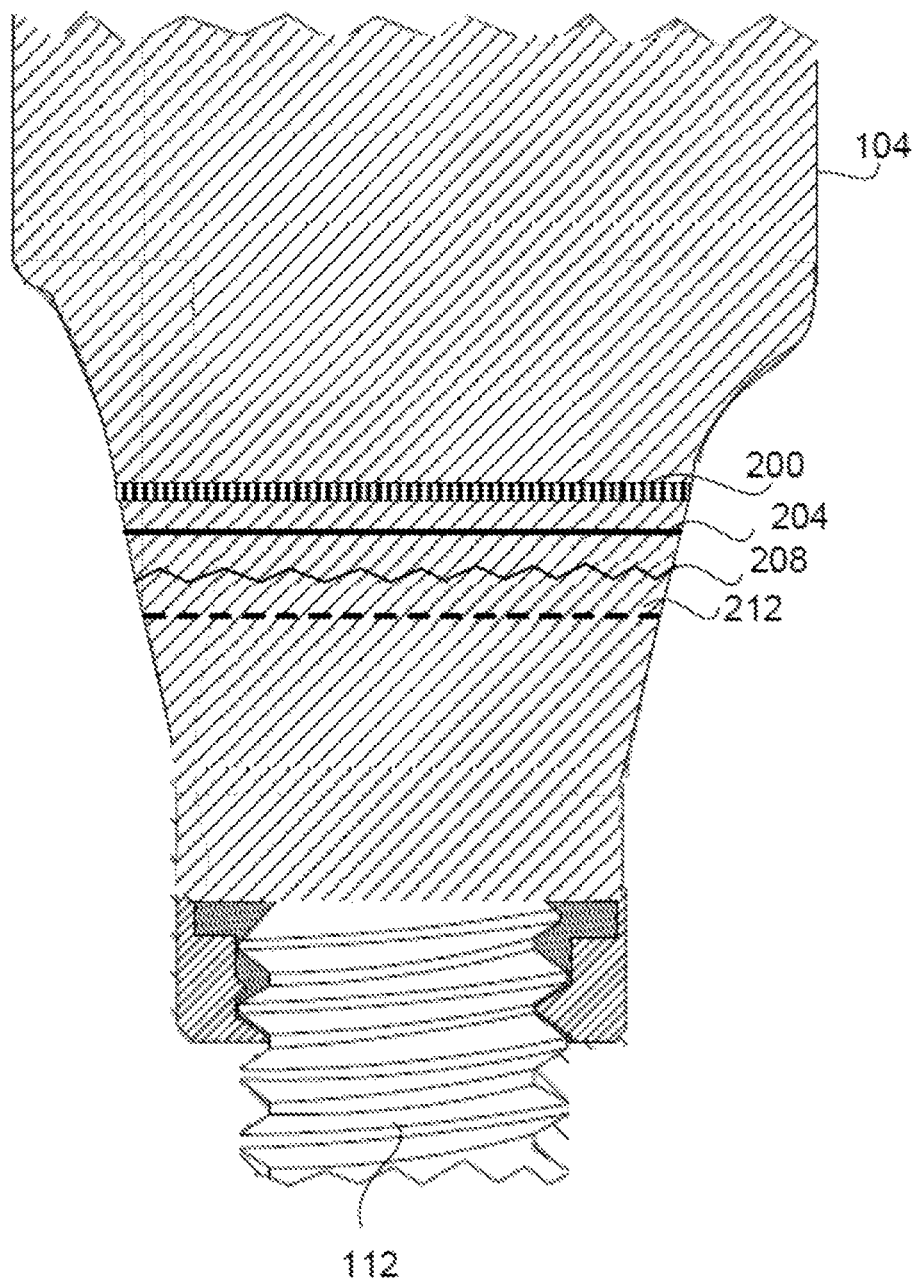
FIG. 2 is a schematic illustration of a frontal view of an abutment, in accordance with some exemplary embodiments of the disclosed subject matter.

Referring now to FIG. 2, showing a schematic illustration of a frontal view of an abutment, in accordance with some exemplary embodiments of the disclosure. Abutment 104 provides for inserting a screw 112 having a main column 112' (not shown). Abutment 104 has thereon a radial or substantially radial mark, such as band mark 200 made of a strip of a different material than abutment 104, continuous line mark 204 which may be implemented as engraving on abutment 104, zigzag line 208, dashed line 212, or the like. Thus, the mark may be made of any structure or material, as long as it is visible in an image taken by available imaging equipment, such as an x-ray image. It will be appreciated that if the mark is made of different material, it should be adjusted into the abutment so that no gaps are formed therebetween. Such materials may include any radio-opaque material which can be applied to titanium.

Figure 3:
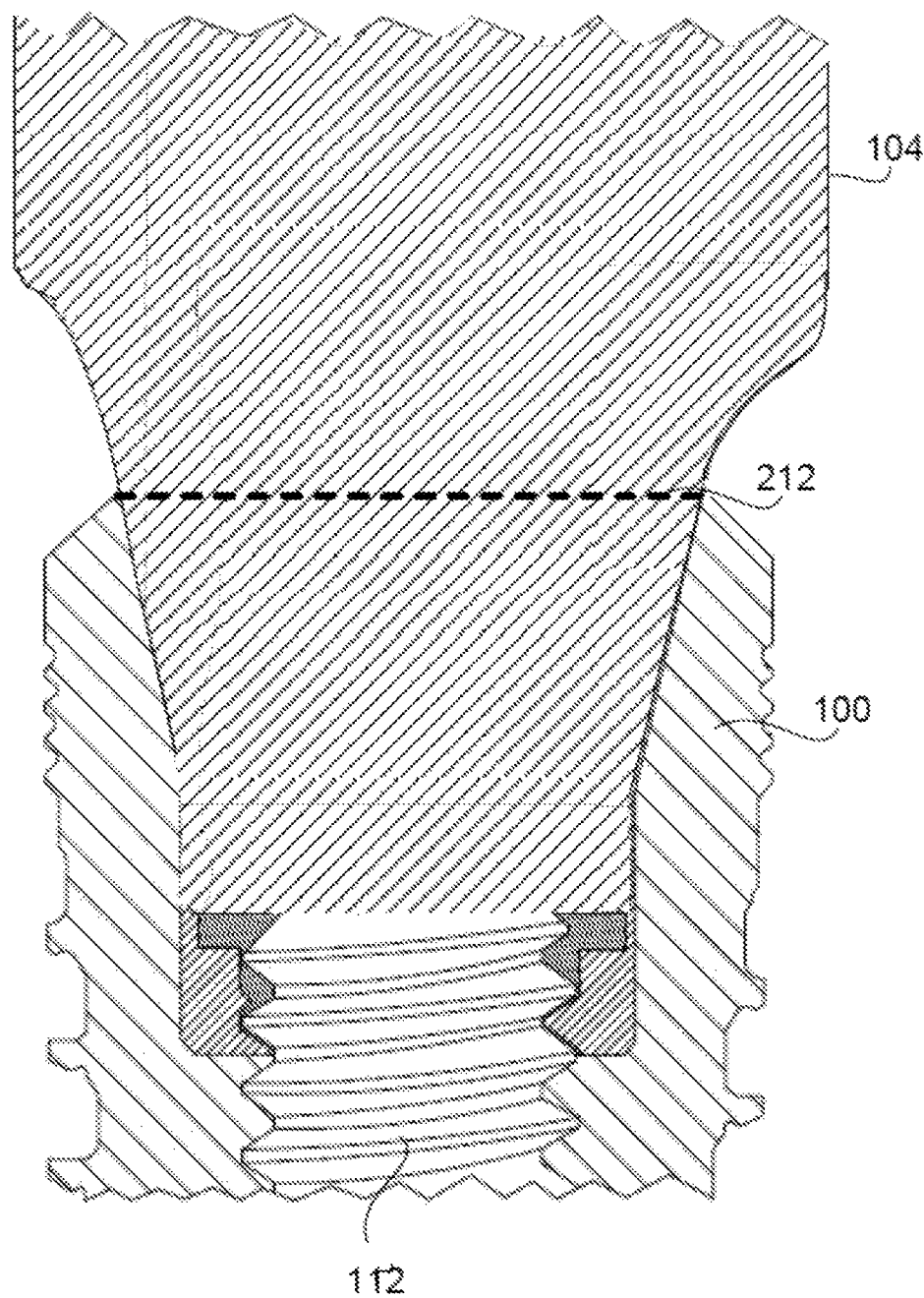
FIG. 3 is a schematic illustration of a frontal view of an implant and properly inserted abutment, in accordance with some exemplary embodiments of the disclosed subject matter.

Referring now to FIG. 3, showing a schematic illustration of a frontal view of an implant and a properly inserted abutment. FIG. 3 shows implant 100, abutment 104 and screw 112, wherein abutment 104 comprises radial mark 212. After the physician inserted the abutment into the implant and screwed screw 112 as required, the physician may then take a frontal image of the relevant teeth, for example using an imaging device. If the abutment is inserted as required, the mark will appear at the correct level, for example it may be on the same level as the opening of the implant.

Once the abutment is inserted and the screw is screwed properly, the crown may be positioned on the screw.

Figure 4A:
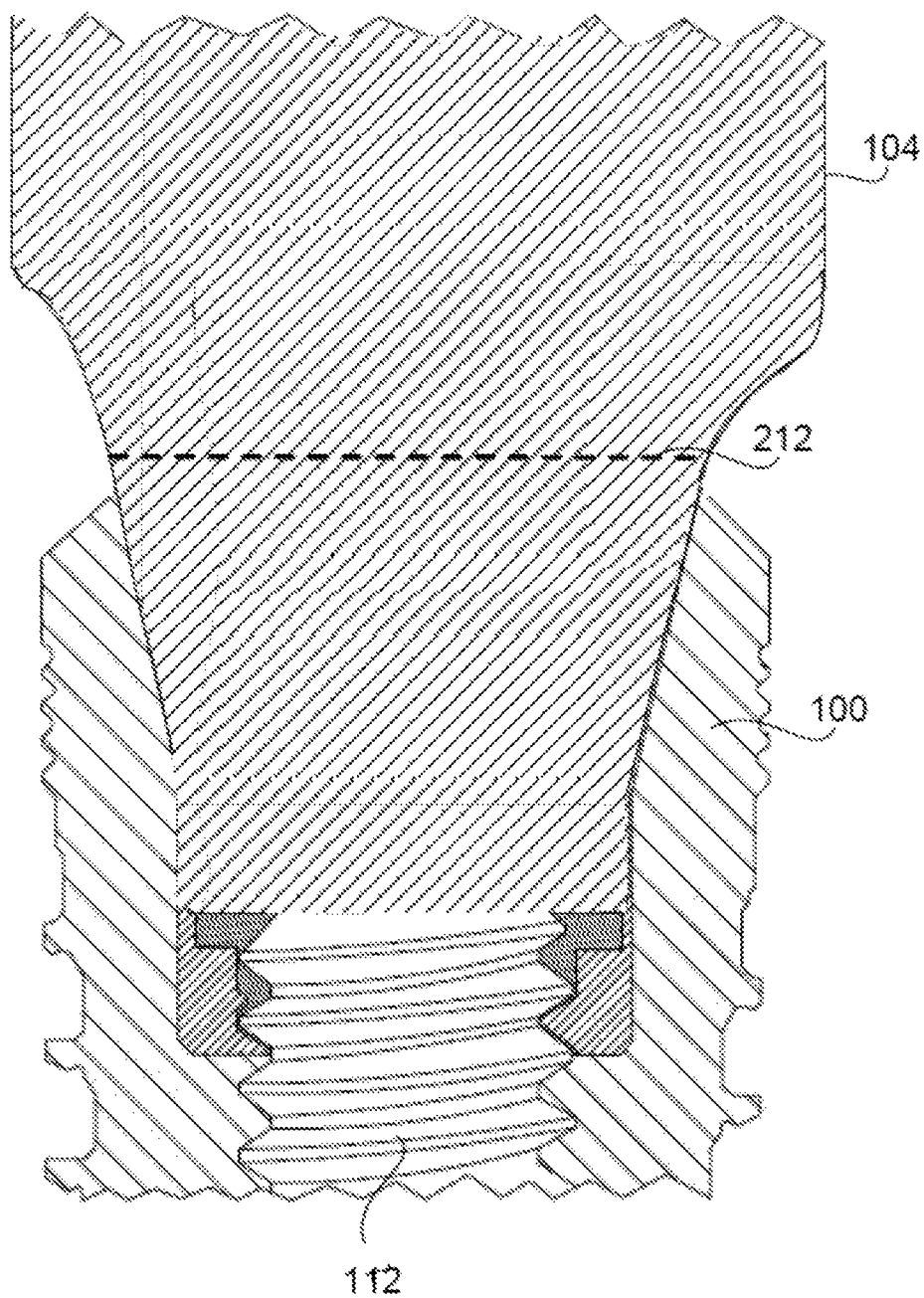
FIGS. 4A and 4B are schematic illustrations of a frontal image of an implant and improperly inserted abutment, in accordance with some exemplary embodiments of the disclosed subject matter.

Referring now to FIG. 4A showing a schematic illustration of a frontal image of an implant and an improperly inserted abutment. In FIG. 4A, abutment 104 and screw 112 are inserted into implant 100. However, the abutment was not inserted deep enough or screw 112 was not screwed enough, such that mark 212 is external to the opening of the implant. In this case, the installing physician may further screw in screw 112, such that the abutment is inserted deeper, until mark 212 is aligned with the opening of the implant.

Figure 4B:
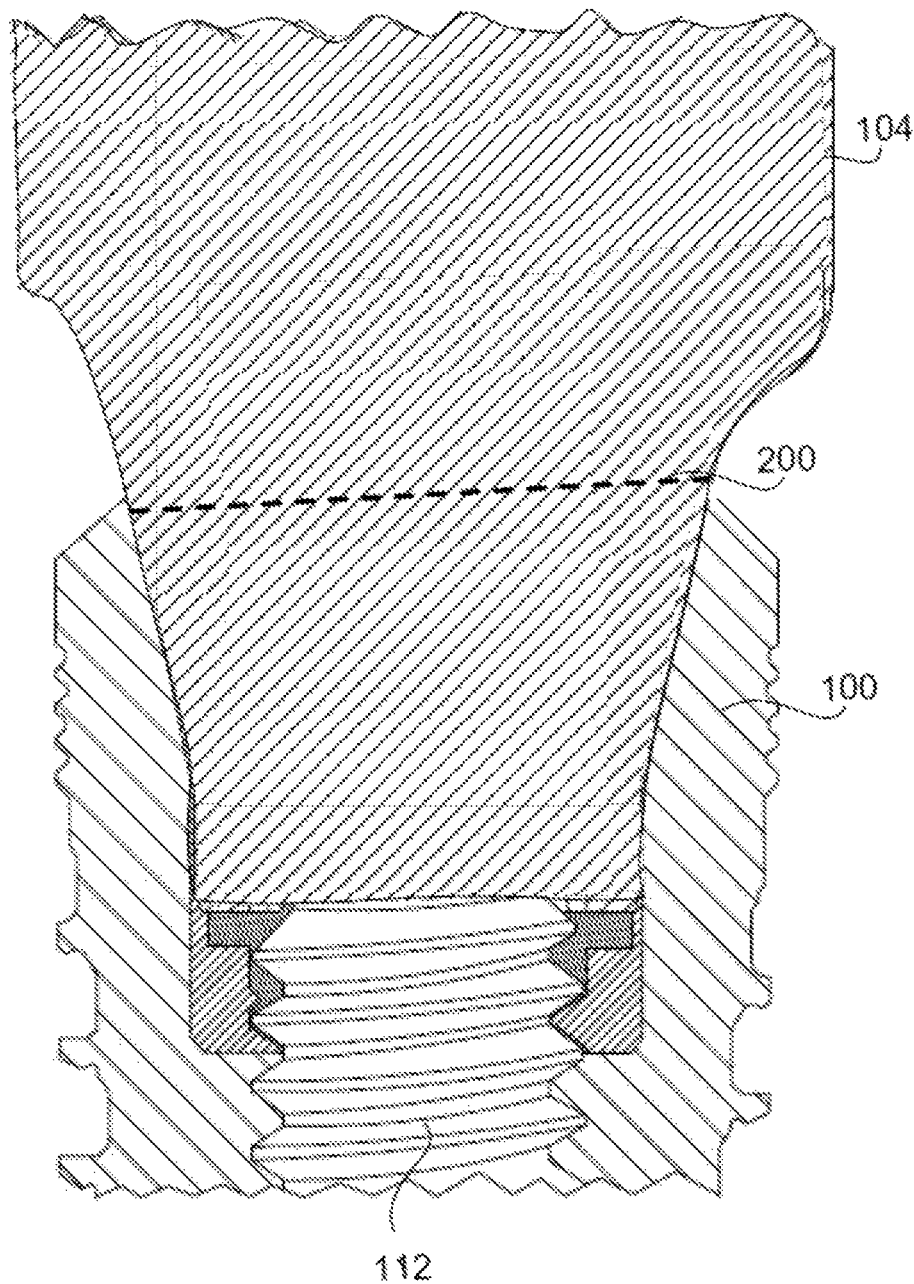

FIG. 4B shows another schematic illustration of a frontal image of an implant and an improperly inserted abutment. In FIG. 4B, abutment 100 and screw 104 is inserted into implant 100, but rather in an angle and not at the required perpendicular position. In this case, the installing physician may unscrew screw 104, remove the abutment, re-insert it and screw in screw 104 properly.

Figure 5:
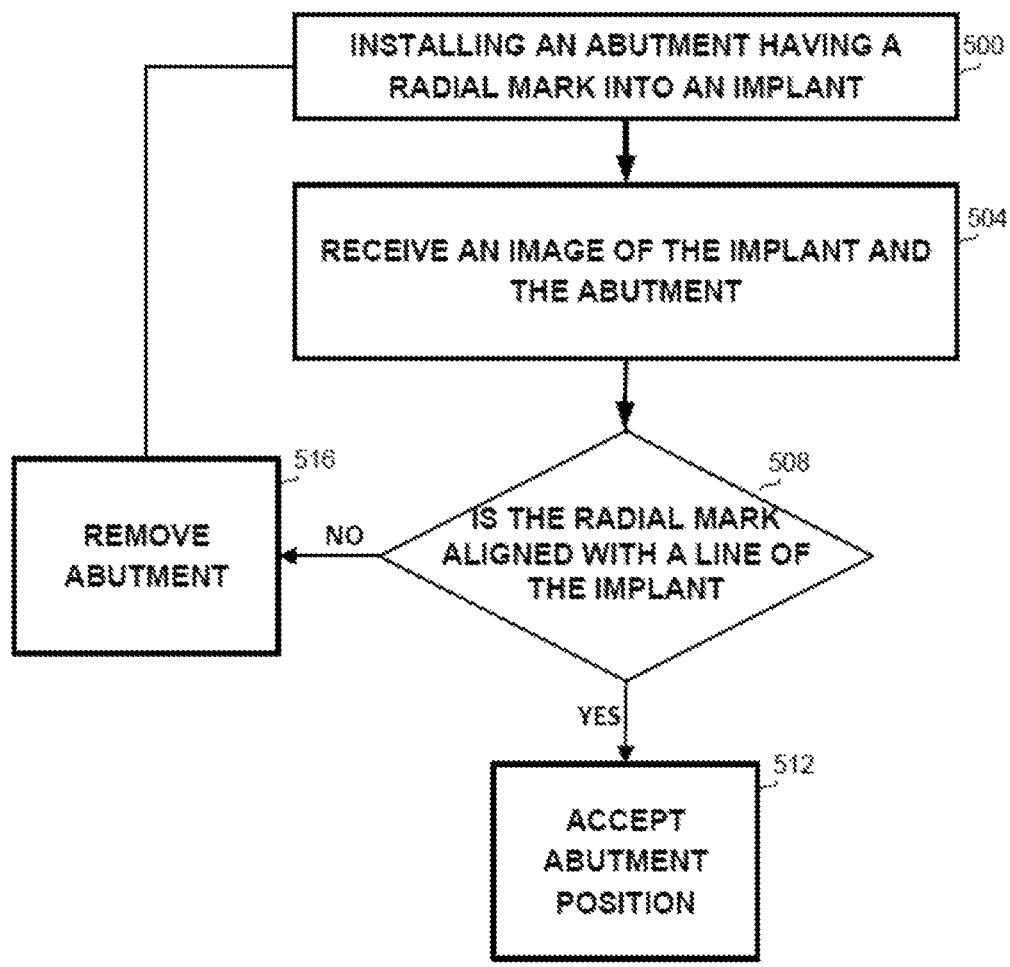
FIG. 5 is a flowchart of steps in a method for installing an abutment, in accordance with some exemplary embodiments of the disclosed subject matter.

Referring now to FIG. 5, showing a flowchart of steps in a method for installing an abutment.

On step 500 A physician or anther dental caregiver may install an abutment into an implant placed in a patient's jaw and screw in a screw 112 to connect abutment 104 to implant 100. The abutment has thereon a radial mark or a radial addition made of another pattern or material, such that it is distinguishable from the rest of the abutment.

On step 504, the physician may receive an image of the implant and the abutment. The image may be an X-ray or another image. The image should be a frontal image, showing the external part of the abutment.

On step 508, it is determined whether the radial mark is aligned with a predetermined level on the implant, such as the opening of the implant, or a line, a mark or an addition located on the external part of the implant.

If the radial mark is aligned with the predetermined radial line on the implant, then on step 512 the abutment position is accepted and the caregiver may proceed. Otherwise, on step 516 the caregiver may unscrew the screw, optionally remove the abutment, and restart inserting again on step 500, whether with the same abutment or screw or with different ones.

It will be appreciated that in other embodiments, the implant may also comprise one or more substantially horizontal marks, and the abutment should be inserted such that the mark on the abutment's wrapping member 104 is aligned with the mark on the implant, rather than with the external part of the opening of the implant. The mark on the implant may be radial, or may be only on the side of the implant which faces forward when installed in the patient's jaw.

It will also be appreciated that an abutment having a mark to be aligned with a mark or a known line in an implant may be implemented also for other abutments and not necessarily to conical abutments.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A dental device, comprising:
an abutment comprising:
   a conical abutment body having
      a lower portion, a neck portion and an upper portion, the neck portion extending upwardly from the lower portion to the upper portion and having a slope shape, the upper portion having a larger diameter than the neck portion, and
      a substantially circumferential mark located on an outer surface of an external part of the neck portion; and
an implant;
wherein the conical abutment body is configured to be connected by a conical connection to the implant by a screw,
wherein the part of the neck portion with the substantially circumferential mark is outside the implant,
wherein the lower portion of the abutment and the part of the neck portion not having the substantially circumferential mark is seated within the implant,
wherein the substantially circumferential mark is distinguishable from the abutment body in an image taken by an imaging device when the implant and abutment are installed,
wherein the substantially circumferential mark is located above the top of the implant, so that the substantially circumferential mark is configured to indicate alignment of the abutment body relative to opening of the implant, and
wherein the screw is configured to be inserted into the implant through a bottom end of the abutment body and adjust the alignment of the abutment body perpendicularly relative to the implant according to horizontal leveling and depth of the substantially circumferential mark relative to the opening of the implant.

2. The dental device of claim 1, wherein the substantially circumferential mark comprises a band made of a different material than the abutment body.

3. The dental device of claim 1, wherein the substantially circumferential mark comprises engraving in the abutment body.

4. The dental device of claim 1, wherein the substantially circumferential mark indicates a required height of the abutment body relative to the opening of the implant when the dental abutment body is inserted properly into the implant and leveled with the implant.

5. The dental device of claim 1, wherein the substantially circumferential mark is aligned with a level of an opening in the implant.

6. The dental device of claim 1, wherein the substantially circumferential mark is aligned with a substantially horizontal mark on an external part of the implant.

7. The dental device of claim 1, wherein the substantially circumferential mark is distinguishable from the abutment body in an image taken by an X-ray imager when the implant and abutment are installed.

8. A method for installing an abutment in a dental implant, comprising:

placing an abutment comprising a conical abutment body and a substantially circumferential mark on its external part, located at outer surface of a slope shaped neck portion of the abutment body, into an implant and connecting the conical abutment to the implant by a screw so a lower portion of the abutment body is entirely seated within the implant, wherein the substantially circumferential mark is configured to indicate alignment of the abutment body relative to opening of the implant, wherein the part of the neck portion with the substantially circumferential mark is outside the implant, and wherein the part of the neck portion not having the substantially circumferential mark is seated within the implant;

receiving an image of the implant and conical abutment;

determining whether the substantially circumferential mark is aligned with a line of the implant; and responsive to the circumferential mark not being aligned with the line of the implant, removing the conical abutment body, wherein the screw is configured to be inserted into the implant through a bottom end of the abutment and adjust the alignment of the abutment body perpendicularly relative to the implant according to horizontal leveling and depth of the substantially circumferential mark relative to the opening of the implant.

9. The method of claim 8, wherein the circumferential mark comprises a band made of a different material than the abutment body.

10. The method of claim 8, wherein the circumferential mark comprises engraving in the abutment body.

11. The method of claim 8, wherein the circumferential mark is aligned with a line of the implant when the abutment is inserted properly into the implant.

12. The method of claim 8, wherein the circumferential mark indicates a level of an opening in the implant.

13. The method of claim 8, wherein the line of the circumferential mark is a substantially horizontal mark on an external part of the implant.

14. The method of claim 8, wherein the imaging device is an X-ray imager.

15. The dental device of claim 1, wherein the circumferential mark allows for verifying that the abutment is inserted at the correct depth within the implant.

16. The dental device of claim 1, wherein the circumferential mark allows for verifying that the abutment is leveled within the implant.

17. The dental device of claim 1, wherein the circumferential mark is engraved on the external part of the abutment or is made of a different material attached to the abutment.

18. The dental device of claim 1, wherein the circumferential mark is shaped as a line surrounding the neck portion of the abutment body, a strip surrounding the abutment, a dashed line surrounding the abutment, a wave surrounding the abutment or a zigzag surrounding the abutment.

19. The dental device of claim 1, wherein the circumferential mark appears in color.

* * * * *